United States Patent [19]

Kessler et al.

[11] 4,242,239
[45] Dec. 30, 1980

[54] BONDABLE AGAR DENTAL IMPRESSION MATERIAL

[75] Inventors: Henry A. Kessler, Succasunna; Richard A. McEvoy, Lincoln Park, both of N.J.

[73] Assignee: Warner-Lambert, Morris Plains, N.J.

[21] Appl. No.: 47,432

[22] Filed: Jun. 11, 1979

[51] Int. Cl.$^3$ .............................................. C08L 5/12
[52] U.S. Cl. .................................. 260/9; 106/38.5 D
[58] Field of Search ........................... 260/9, 998.11; 106/38.5 D

[56] References Cited

U.S. PATENT DOCUMENTS

| 2,021,058 | 11/1935 | Harrison | 106/38.5 D |
| 2,089,552 | 8/1937 | Harrison | 106/38.5 D |
| 2,234,383 | 3/1941 | Preble | 106/38.5 D |
| 2,422,497 | 6/1947 | Noyes | 106/38.5 D |
| 2,526,043 | 10/1950 | Parr et al. | 106/38.5 D |
| 4,060,421 | 11/1977 | Yoshikawa | 106/38.5 D |

FOREIGN PATENT DOCUMENTS 1073772 6/1967 United Kingdom ............... 106/38.5 D Primary Examiner—Edward M. Woodberry
Attorney, Agent, or Firm—Albert H. Graddis; Stephen Raines

[57] ABSTRACT

A heavy bodied reversible hydrocolloid dental impression material is disclosed. This material comprises agar-agar as the main component in which there is added a small amount of locust bean gum, potassium or zinc sulfate, a borate and nonionic poly(ethyleneoxide)-homopolymer. This dental impression material is effective, for example, for bonding to an alginate material.

4 Claims, No Drawings

BONDABLE AGAR DENTAL IMPRESSION MATERIAL

BACKGROUND OF THE INVENTION

This invention relates to a composition of matter and more particularly relates to an improved dental impression material exhibiting excellent flow characteristics and superior bonding capability to alginate or irreversible hydrocolloid dental impression materials.

Agar-agar based dental impression system is known in the art. See, for example,

Preble, B., U.S. Pat. No. 2,234,383, Mar. 11, 1941; Skinners Science of Dental Materials, p. 107-108, 7th Edition, 1973, and Phillips, R. W., et al., Materials for the Practicing Dentist, p. 106, 1969.

Essentially, this system comprises agar-agar as the main ingredient in an aqueous vehicle. Later references such as Igarashi, T, et. al., Bull. Tokyo Dent. Coll., 18 (2) 47–56, May 1977; and Yoshikawa et. al., U.S. Pat. No. 4,060,421, Nov. 29, 1977; describe an agar-agar system in which the agar-agar system includes agents such as borates and sulfates. These references are incorporated herein by reference.

In the prior art techniques, the agar-agar base hydrocolloid dental impression material is ejected from a syringe. The material after liquefication and heated to a temperature of about 150° F. is pushed through a 19 guage needle onto or about the tooth structures, teeth or parts of the oral cavity. The second dental impression material comprising essentially an alginate or irreversible hydrocolloid impression material may serve as the tray material. The alginate is kept at a temperature below the solidification temperature of the agar material. The covering of the agar based dental system prior to its gelation, by the alginate results in a rapid solidification of the agar syringe material. Thus, this technique eliminates the need of subjecting the agar material to a tempering bath for the purpose of lowering the temperature of the agar material from 150° F. to 110° F. to 120° F.

The agar based impression material of prior art suffers from several drawbacks. The main drawback is that the agar material is extremely fluid resulting in the gel having very little body. Because of the fluid nature of this preparation, it is difficult to cover a large mouth area. For example, in some instances, because of the fluidity, the material barely covers the fourth prepared tooth. Furthermore, because of the fluidity of the agar system, it is readily displaced by the second alginate impression material resulting in the formation of a very thin agar impression which is highly undesirable.

SUMMARY OF THE INVENTION

One object of the present invention is to provide an agar based dental impression material which has a heavy body yet exhibiting consistent flow properties.

Another object of the present invention is to provide an agar material which can be readily ejected from a 19 gauge needle and coalesce into a homogeneous mass against the teeth and other oral tissues.

Yet another object of the present invention is to provide an agar base material having a high compressive strength such as from about 3,500 to 6,000 g/cm$^2$.

A further object of the present invention is to provide a dental impression material which comprises agar-agar as the main component from which inlays, crowns, bridges and partial dentures are developed.

Yet another object of the present invention, is to provide a bondable agar-agar system comprising a mixture of agar, potassium or zinc sulfate, locust bean gum a borate and poly(ethylene oxide) polymer having the following repeating unit:

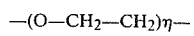

in water. When such a system is combined with an alginate system, a superior impression is obtained with the agar system bonding to the alginate material.

DETAILED DESCRIPTION OF THE INVENTION

According to the present invention, there is provided an improved agar-agar dental impression material. The improvement comprises adding to known agar-agar impression materials a small amount of poly(ethylene oxide) homopolymer. Thus, in a typical embodiment of the present invention, about 0.1%–1.0% by weight of poly(ethylene oxide) homopolymer are added to an agar-agar system. The agar-agar system comprises about 11.20% by weight of agar, about 0.2%–0.5% by weight of any water soluble borate, about 3.0% by weight of potassium or zinc sulfate, the remaining being water to make up 100%.

This material exhibits excellent flow characteristics and when it is placed in contact with an alginate system, a resilient gel is formed. This gel exhibits high compressive strength about 3,500 to 6,000 g/cm$^2$. The poly(ethylene oxide) homopolymer which can be advantageously employed in the present invention are those homopolymers having a molecular weight of approximately 100,000 to 5,000,000. This material is available commercially under the trade name Polyox WSR-301 from Union Carbide. The material having a molecular weight of 4,000,000 is preferred. With respect to the borate, any soluble borate, organic or inorganic, may also be advantageously used. Typically, calcium, potassium, or sodium borate may be advantageously employed. To enhance the viscosity of the resulting system, a small amount such as from about 0.1% to 0.75% by weight of locust bean gum may be optionally included in the agar-agar system.

To improve the aesthetic value of prepared material, optional agents such as small amounts of opacifiers, flavor, and colorants may be added thereto. These agents are known in the art. See for example those disclosed in the foregoing references.

In a typical commercial embodiment of the present agar-agar impression material, the ingredients are mixed in water with the aid of heat such as from 85° C. to 95° C. The hot material is pumped into suitable packaging containers.

In use, the dental practitioner injects the bondable agar-agar system of the present invention onto the area on which the impression is to be taken. A solid gel is formed when known alginate system is placed in contact with the agar-agar system and the agar impression material adheres to the alginate system.

EXAMPLE 1

The following is an example of the components in the reversible hydrocolloid dental impression material. The method of preparation is known in the art. The agar is added to water for the purpose of wetting the agar.

Subsequently the temperature is raised to 85° to 95° C. to facilitate the dissolution of the agar. This is achieved using a steam jacketted stainless steel mixing vessel. The other ingredients are added to the agar sol. The hot material is then pumped into suitable packaging containers.

| | |
|---|---|
| Calcium Borate | 0.30% |
| Opacifiers | 0.90% |
| Preservative | 0.20% |
| Agar-Agar | 11.20% |
| Locust Bean Gum | 0.30% |
| Poly (ethylene Oxide) Polymer | 0.50% |
| Potassium/Zinc Sulfate | 3.00% |
| Flavor | 0.87% |
| Colorant | 0.30% |
| Water to make | 100% |

We claim:

1. In an improved agar-agar dental impression material, the improvement comprises the inclusion of a small amount of a poly(ethylene oxide) polymer having a molecular weight of about 100,000 to about 5,000,000.

2. The dental impression material of claim 1 in which the poly(ethylene oxide) homopolymer is present at a concentration of 0.1% by weight–1.0% by weight.

3. The dental impression material as claimed in claim 1, wherein there is included locust bean gum at a concentration of 0.1%–0.75% by weight.

4. An improved agar-hydrocolloid dental impression material comprising about 11.20% by weight of agar-agar, 0.30% by weight of locust bean gum, 0.50% by weight of poly(ethylene oxide) homopolymer having a molecular weight of about 4,000,000, 3.00% by weight of potassium or zinc sulfate, 0.30% by weight of calcium borate and sufficient water to make 100%.

* * * * *